United States Patent [19]

Sloma et al.

[11] Patent Number: 5,763,187
[45] Date of Patent: Jun. 9, 1998

[54] BACTERIAL DONOR CELL USEFUL IN CONJUGATION

[75] Inventors: Alan P. Sloma; William R. Widner, both of Davis, Calif.

[73] Assignee: Novo Nordisk Biotech, Inc., Davis, Calif.

[21] Appl. No.: 785,448

[22] Filed: Jan. 17, 1997

Related U.S. Application Data

[60] Provisional application No. 60/010,239 Jan. 19, 1996.
[51] Int. Cl.$^6$ .............. C12Q 1/68; C12P 21/00; C12N 15/65; C07H 21/04
[52] U.S. Cl. ............ 435/6; 435/71.2; 435/252.31; 435/252.5; 435/320.1; 536/23.7
[58] Field of Search ............... 435/6, 69.1, 71.2, 435/91.4, 252.31, 252.5, 320.1; 536/23.7

[56] References Cited

U.S. PATENT DOCUMENTS 5,346,818  9/1994  Schäfer et al. ................ 535/172.3

FOREIGN PATENT DOCUMENTS

WO 96/29418  9/1996  WIPO.

OTHER PUBLICATIONS

Slepecky et al. The genus Bacillus–nonmedical. in: The prokaryotes, 2nd ed., Eds. Balows, Truper, Dworkin, Harder and Schleifer, Springer–Verlag. vol. 2:1663–1693, Dec. 1991.

Hendrick et al. Insertino of Tn916 into *Bacillus pumilus* plasmid pMGD302 adn evidence for plasmid transfer by conjugation. Plasmid vol. 26:1–9, Sep. 11, 1991.

Jacobs et al. *Bacillus subtilis* PrsA is required in vivo as an extracytoplasmec chaperone for secretin of active enzymes synthesized either with or without pro–sequences. Mol. Microbiol. vol. 8(5):957–966, May 1993.

Selinger et al. Mobilization of closely related plasmids pUB110 and pBC16 by Bacillus plasmid pXO503 requires trans–acting open reading frame beta. J. Bact. vol. 172(6):3290–3297, Jun. 1990.

*Primary Examiner*—Nancy Degen
*Assistant Examiner*—William Sandals
*Attorney, Agent, or Firm*—Steve T. Zelson, Esq.; Elias J. Lambiris, Esq.

[57] ABSTRACT

The present invention relates to a modified bacterial donor cell useful in conjugation, the cell containing i) a plasmid comprising a DNA construct encoding the polypeptide of interest, and at least one cis-acting DNA sequence required for the transfer of said plasmid by conjugation in the presence of a trans-acting mobilizing element, and ii) at least one DNA sequence encoding said trans-acting mobilizing element, wherein the donor cell has a reduced capacity, relative to a parent cell, of producing a bactericidal agent which kills or prevents growth in a population of recipient cells.

24 Claims, No Drawings

BACTERIAL DONOR CELL USEFUL IN CONJUGATION

This application is a continuation-in-part of application Ser. No. 60/010,239, filed Jan. 19, 1996 now abandoned, the contents of which are herein incorporated by reference.

FIELD OF THE INVENTION

The present invention relates to the field of introduction of DNA into cells of *Bacillus spp.* and of the production of polypeptides by cultivation of such cells. In particular, the invention is directed to cells modified for use as donor cells in Bacillus conjugation.

BACKGROUND OF THE INVENTION

Traditionally, three different methods have been used for introducing DNA into strains of *Bacillus sp.* The first method, which is generally useful only for cells of *B. subtilis*, is transformation of competent cells, the second is based on the principles of electroporation, and the third is based on transformation of protoplasts.

Especially the protoplast transformation and the transformation of competent cells are widely used. However, while protoplast transformation functions for a number of different *Bacillus sp.* it cannot, in general, be accomplished in less than several days, which makes this method cumbersome to use. Furthermore, as mentioned above, transformation of competent cells has generally only been shown to work satisfactorily for cells of *B. subtilis* 168.

It has been shown that some strains of Bacillus may take up DNA by means of conjugation, i.e. by exchange of genetic material mediated by certain "transfer plasmids".

More specifically, Koehler and Thorne (in Journal of Bacteriology, November 1987, pp. 5771–5278) describe a 55 kb plasmid, pLS20, which is capable of mediating transfer of plasmids between *Bacillus sp.* The transfer of the tetracycline resistance plasmid pBC16 and the *Staphylococcus aureus* kanamycin resistance plasmid pUB110, respectively, were shown to be mediated by the plasmid pLS20 from a strain of *B. subtilis* (*natto*) to strains of the *Bacillus spp. B. anthracis, B. cerus, B. licheniformis, B. megaterium, B. pumilus, B. subtilis* and *B. thuringiensis*. Other plasmids were found to be unable to transfer by use of pLS20. The transfer of plasmids mediated by pLS20 was concluded to take place by donation rather than conduction, i.e. without physical association of the two plasmids.

In Journal of Bacteriology, June 1990, pp. 3290–3297 Selinger et al. identify an open reading frame β (ORF-β) region in the nonconjugative plasmids pUB110 and pBC16 and conclude that this region is essential for mobilization of the plasmids by the conjugational plasmid pLS20 or its derivatives. Also another region of pUB110 and pBC16 located 5' to ORF-β (and presumably including oriT) is shown to be necessary for mobilization. ORF-β is acting in trans whereas the other region is cis-acting.

It is an object of the present invention to provide improved systems for introducing DNA into strains of *Bacillus sp.* and to use these systems for the production of polypeptides of interest.

BRIEF DISCLOSURE OF THE INVENTION

It has surprisingly been found that conjugation may be used for introducing DNA encoding a translocated polypeptide into a number of different *Bacillus sp.*, in particular cells of industrial interest, and further that the use of conjugation for this purpose is much more simple and fast than the above mentioned conventionally used methods. In addition, the transfer frequency is much higher than that observed for conventionally used methods. Furthermore, conjugation may be used to introduce DNA into cells for which conventional methods have proved unsatisfactory or simply untenable. The method of conjugation involves utilizing, as a donor cell, a bacterial cell, preferably Bacillus, containing i) a plasmid comprising a DNA construct encoding the polypeptide of interest, and at least one cis-acting DNA sequence required for the transfer of said plasmid by conjugation in the presence of a trans-acting mobilizing element, and ii) at least one DNA sequence encoding said trans-acting mobilizing element. In a preferred embodiment, the protein is a translocated protein.

Notwithstanding the surprising success in use of such donor cells in conjugation, however, in many cases the number of surviving transconjugants is still less than would be desired and/or expected. It has now been unexpectedly found that the low rate of survivorship among recipient cells is due to the production of bactericidal compounds by the donor cells. In this regard, the present invention now provides novel donor cells which, in addition to being adapted for successful conjugation between *Bacillus spp.*, as disclosed above, have been modified in such a way as to improve the survival of the recipient cells after conjugation.

Accordingly, in a first aspect the invention relates to a modified Bacillus donor cell which, in addition to containing the elements required for successful conjugation as defined above, exhibits a reduced capacity, relative to a parent cell strain from which it is derived, for producing a bactericidal agent which kills or prevents the population of recipient cells from growing. "Reduced capacity" in the present context means that, after incubation with the modified donor cells under conjugation conditions, recipient cells exhibit a measurable increase in viability, relative to the viability observed when the parent cell from which it is derived is used in the same conjugation method. In a preferred embodiment, the use of the modified donor cell results in at least about 10% improvement in survival of recipient cells relative to the survival rate when the parent cell from which it is derived is used in the same conjugation method. The invention also relates to a method in which a population of the novel donor cells and a population of *Bacillus sp.* recipient cells are mixed under conditions allowing the plasmid to be transferred from the population of donor cells to the population of recipient cells by conjugation. The recipient cells may, e.g., be cells of industrial or alkalophilic *Bacillus sp.* for which known DNA introduction methods either are non-existing or very laborious.

DEFINITIONS

The term "translocated polypeptide" is intended to indicate that the polypeptide to be expressed carries a signal sequence which enables it to be translocated across the cell membrane. In particular, the translocated polypeptide may be a secreted polypeptide or a polypeptide involved in the secretory machinery of the Bacillus cell in question.

In the present context the term "cis-acting DNA sequence required for the transfer of said plasmid by conjugation in the presence of a trans-acting mobilizing element" is intended to indicate a DNA sequence or DNA site necessary for mobilization to take place, which must be located on the plasmid which is to be introduced into the recipient cell. The cis-acting DNA sequence may be oriT or a functional analogue or part thereof.

The term "trans-acting mobilizing element" is intended to indicate a protein mediating conjugative transfer of DNA sequences containing the cis-acting DNA sequence defined above. The trans-acting mobilizing element may be a protein encoded by a conjugational plasmid, such as pLS20, or a part or derivative thereof, or may be a protein encoded by a DNA sequence such as orf-β or a functional analogue or part thereof. It will be understood that since the mobilizing element is acting in trans it may be encoded by DNA present in the genome of the donor cell or on a second plasmid, such as a conjugative plasmid, present in said donor cell.

DNA sequences comprising oriT and orf-β, respectively, are described by Sellinger et al., op. cit.

The terms "functional analogue" or "functional part" as used about oriT and orf-β, respectively, are intended to indicate that a modified gene sequence may be used as long as the plasmid mobilizing function conferred by the modified gene sequence is not substantially impaired. For instance, it is contemplated that parts of oriT and orf-β (as described by Sellinger et al.), respectively, may exert the desired function. Functional parts or analogues of oriT and orf-β, respectively, may be identified by modifications of the native oriT or orf-β, such as by deletion, insertion or substitution of one or more nucleotides by conventional DNA modification techniques and subsequent testing for plasmid mobilization capability of the resulting part or analogue.

The term "conjugative plasmid" is intended to cover any plasmid which is able to mediate transfer of DNA by conjugation. One very suitable example is the plasmid pLS20 (described by Sellinger et al., op. cit.) or a plasmid essentially identical thereto, or a derivative of pLS20— having retained the plasmid mobilizing capability of pLS20. The term "derivative" as used in connection with the plasmid pLS20 is intended to indicate a genetically modified plasmid, typically reduced in size, which has retained the conjugation mediating capability of said plasmid.

The term "curable plasmid" is intended to indicate that a cell harbouring the plasmid may be cured from said plasmid by an externally applied factor. For instance, the plasmid may carry a conditional origin of replication allowing the plasmid to replicate under certain (permissive) conditions and unable to replicate under other (non-permissive) conditions. The plasmid may, for instance, be one which is temperature-sensitive for replication.

It should be noted that, in the present context, the term "plasmid" is also intended to denote a bacteriophage or other DNA molecule capable of functioning as an autonomously replicating extrachromosomal element, and that reference to a mobilizably plasmid throughout the specification and claims is also intended to encompass any mobilizable genetic element, e.g., a chromosomal DNA sequence or a non-autonomously replicating element, etc.

DETAILED DISCLOSURE OF THE INVENTION

Conjugation by Use of Specific Types of Donor Cells

Although conjugation, as mentioned above, is a much more efficient and generally applicable method for introduction of DNA into recipient bacterial cells than conventional techniques, the conjugation frequency have been found to be relatively low for conjugation between certain types of donor and recipient cells.

The present inventors have now surprisingly found that part of the low conjugation frequency problem is based on the fact that the donor cell produces low amounts of a bactericidal agent which either kills or reduces the growth rate of the recipient cells. Thus, when the production of said bactericidal agent is reduced or eliminated, the conjugation frequency may be increased significantly. To this end, novel donor cells are created by modification of the parent cell to reduce the effect of the bactericidal agent produced by the parent cell.

Accordingly, in a further important aspect the invention relates to a method of constructing a cell of a *Bacillus sp.* harbouring a DNA construct encoding a polypeptide of interest, in which method a population of bacterial donor cells harbouring i) a plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of *Bacillus sp.* recipient cells are mixed under conditions allowing the plasmid to be transferred from the population of donor cells to the population of recipient cells by conjugation, the population of donor cells being prepared from modified cells which have a reduced capability of producing a bactericidal agent which kills or prevents the population of recipient cells from growth.

In the present context, a modified donor cell, which term also encompasses any progeny thereof, is considered to have "reduced capacity" of producing a bactericidal agent if, after incubation with the modified donor cells under conjugation conditions, recipient cells exhibit a measurable increase in viability, relative to the viability observed when the parent cell from which the donor cell was derived is used in the same conjugation method. In one embodiment, the modified donor cell permits survival of at least about 1% more recipient cells than the parent donor cell line from which it was ultimately derived, when both donor cells are used for conjugation under the same conditions and with the same conjugation elements. Preferably, the modified donor cell permits survival of at least about 10% more recipient cells, more preferably 20% more, and most preferably at least about 30% more recipient cells than the parent cell line.

The term "bactericidal agent" is intended to include any component produced by a bacterial cell population which exerts a growth-inhibiting or effect on or killing of the population of recipient cells, the presence of which is not essential for the population of donor cells to exert their conjugation mediating activity. It will be understood that the native donor cell may produce more than one bactericidal agent and in accordance with this aspect of the invention, the term "reduced production of a bactericidal agent" is intended to mean that the total amount or number of different active bactericidal agent(s) produced by the population of donor cells has been reduced. In other words, the term connotes that the population of donor cells is deficient in or produces a reduced amount of one, two or more bactericidal agents.

The method according to this aspect of the invention is believed to be useful in connection with any bactericidal agent, i.e. any component produced by the population of donor cells which exhibits a growth-inhibiting or killing effect on the population of recipient cells. It will be understood that the relevant bactericidal agent(s) to be reduced or eliminated will depend on the recipient cell of choice. In the examples hereinafter it is shown that different *Bacillus sp* are sensitive towards different bactericidal agents and that the conjugation frequency may be significantly increased by reducing or eliminating the production of more than one type of bactericidal agent (which need not be characterized in any other detail than its growth-inhibiting or killing effect on the recipient cell of choice).

The term "modified donor cells" encompasses cells produced by deletion or inactivation of selected genes involved in the production of a specific bactericidal agent from the donor cell (such as bacilysin in the case of *B. amyloliquefaciens* and *B. lentus* recipient cells), as well as cells known to have been modified so as to reduce or eliminate a bactericidal agent, which cell is further modified to incorporate the elements required for conjugation in accordance with the disclosure herein. A generally more applicable method is to subject the parent donor cell to mutagenesis and select for mutant cells which exhibit a lower degree of killing or growth-inhibition of the bacterial recipient cells than the parent cells or no killing. Normally, the selection will be performed by replicating colonies of mutagenized cells onto a freshly spread lawn of the "sensitive" recipient cells, identifying colonies which have reduced or preferably no zone of killing surrounding them. In a similar fashion, a parent donor cell population, which has not been deliberately exposed to a mutagen, may be simply screened for naturally occurring variants which exhibit the reduced capacity for killing recipient cells; in the present specification and claims, it will be understood that the term "mutagenizing" also encompasses this method of isolating "modified" cells as well.

The mutagenesis may, e.g., be performed by use of a suitable physical or chemical mutagenizing agent, by use of a suitable oligonucleotide, or by subjecting the DNA sequence to PCR generated mutagenesis, the latter possibilities being of particular relevance when a DNA sequence encoding the bactericidal agent in question or otherwise, involved in the production in said agent is known. Furthermore, the mutagenesis may be performed by use of any combination of these mutagenizing agents.

Examples of a physical or chemical mutagenizing agent suitable for the present purpose includes ultraviolet (UV) irradiations, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions for the mutagenesis to take place, and selecting for mutated cells having a reduced production of the bactericidal agent. In practice, the selection will be performed by replicating colonies of mutagenized cells onto a freshly spread lawn of the "sensitive" recipient cells, identifying colonies which have reduced or preferably no zone of killing surrounding them.

When the DNA sequence encoding the bactericidal agent or is involved in the production of said agent is known, the modification or inactivation may be accomplished by introduction, substitution or removal of one or more nucleotides in the DNA sequence encoding the bactericidal agent or an enzyme involved in its synthesis or in a regulatory element required for the transcription or translation thereof, nucleotides may, e.g., be inserted or removed so as to result in the introduction of a stop codon, the removal of the start codon or a change of the open reading frame. The modification or inactivation of the DNA sequence or a regulatory element may be accomplished by site-directed mutagenesis or PCR generated mutagenesis in accordance with methods known in the art. Convenient techniques include gene disruption or gene replacement or antisense.

The bactericidal agent may, e.g., be an antibiotic such as bacilysin which is known to be produced by certain strains of *B. subtilis* such as *B. subtilis* 168. Bacilysin deficient *B. subtilis* cells exist and can be chosen as donor cells for the introduction of DNA by conjugation in accordance with the present invention. Another bactericidal agent is subtilosin which is also produced by *B. subtilis* 168.

In addition to having a reduced production of a bactericidal agent, the donor cell may carry any of the other traits which are advantageous for conjugation to take place. For instance, the donor cell may be auxotrophic as described in further detail above.

Production of Useful Recipient Cells

An alternate method for improving the frequency of success in conjugation is to use a population of recipient cells which are refractory to killing by the donor cell. In many cases, however, the recipient cell of interest will not have this trait. In order to be able to use the recipient cell of interest, it is possible by screening to isolate cells from the susceptible population which may survive exposure to the donor cells. To achieve this, the donor cells are mixed with mutagenized recipient cells, for a time and under conditions which normally permit killing or growth inhibition to take place. Surviving cells from the recipient cell population are then isolated and cultured, to provide a recipient cell population which can be used successfully in the conjugation process, even with an unmodified donor cell. It will be understood that when the term "mutagenized" is used in connection with recipient cells, it refers both to cells which have been actively mutagenized, in the manner disclosed above for donor cells, as well as to naturally occurring mutants which may exist among the recipient cell population.

Production of a Translocated Polypeptide

The donor cells are useful in conjugation with recipient cells, which in turn are used to produce polypeptides, preferably translocated polypeptides, by cultivation of a cell of a recipient Bacillus cell which through conjugation has acquired a DNA construct encoding the translocated polypeptide in question. The conjugation is preferably accomplished by use of a plasmid carrying the DNA construct and at least one cis-acting sequence required for transfer of said plasmid by conjugation in the presence of at least one mobilizing element, the mobilizing element being provided in trans, i.e. by any of the method of conjugation which are described in much further detail in the following disclosure.

One type of Bacillus strains of particular interest in connection with the present invention is alkalophilic Bacilli. Examples of alkalophilic *Bacillus sp.* include those described in U.S. Pat. No. 5,217,878, e.g., *Bacillus sp.* BP92, U.S. Pat. No. 3,723,250 and U.S. Pat. No. 3,840,433.

Another type of Bacillus strain of interest for the present method is a cell of an industrial Bacillus. The term "industrial *Bacillus sp.*" is intended to indicate a non-recombinant strain of a *Bacillus sp.* different from *Bacillus subtilis* 168, which is capable of producing more than 5 g/l of a secreted polypeptide.

Examples of industrial *Bacillus sp.* are specified in EP 134 048 and include strains of *B. licheniformis, B. amyloliquefaciens* and *B. lentus*.

Further examples of suitable cells of Bacillus (which may or may not be industrial and/or alkalophilic) may be selected from the group consisting of *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium,* and *Bacillus thuringiensis.*

In order improve the stability of the Bacillus cell to be used in the method according to this aspect of the invention, it is desirable that the DNA construct encoding the translocated polypeptide is integrated into the genome of the Bacillus cell. This may be accomplished when the plasmid carries one or more DNA sequences which are sufficiently homologous to a part of the genome of the recipient cell to allow for homologous recombination. Suitable methods for obtaining stable integration of the DNA construct in the genome of the recipient cell are discussed in further details below.

The translocatable polypeptide to be produced in accordance with the method of the first aspect of the invention is preferably a secreted polypeptide or a polypeptide of the secretory pathway of a secreting cell.

The secreted polypeptide may be an enzyme, e.g., selected from an amylolytic enzyme, a lipolytic enzyme, a proteolytic enzyme, a cellulytic enzyme, an oxidoreductase or a plant cell-wall degrading enzyme. Examples of such enzymes include AMG, amylase, lipase, cutinase, esterase, cellulase, hemicellulase, protease, peroxidase, laccase, phenoloxidase, catalase, glucose oxidase, phytase, lyase, pectinase, glucosidase, mannosidase, isomerase, invertase, trasferase, ribonuclease, galactosidase and chitinase. Alternatively, the secreted polypeptide may be a hormone, a growth factor, a receptor or the like.

A preferred example of a polypeptide of the secretory pathway is PrsA (WO 94/19471, the content of which is incorporated herein by reference).

When the translocated polypeptide is a secreted protein the method of this first aspect of the invention preferably further comprises a polypeptide recovery step. The polypeptide may be recovered by conventional procedures including separating the cells from the medium by centrifugation or filtration, if necessary after disruption of the cells, precipitating the proteinaceous components of the supernatant or filtrate by means of a salt, e.g., ammonium sulphate, followed by purification by a variety of chromatographic procedures, e.g., ion exchange chromatography, affinity chromatography, or the like.

Methods of the Invention for DNA Introduction by Conjugation

Using an Industrial Bacillus or an Alkalophilic Bacillus Recipient Cell

In a preferred embodiment of the invention, the donor cell is used in a method of introducing a DNA construct encoding a polypeptide of interest into a cell of a *Bacillus sp.,* in which method a population of bacterial donor cells harbouring i) a plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of *Bacillus sp.* recipient cells are mixed under conditions allowing the plasmid to be transferred from the population of donor cells to the population of recipient cells by conjugation, the *Bacillus sp.* being an alkalophilic *Bacillus sp.* and/or an industrial *Bacillus sp.*

This aspect of the invention is particularly advantageous since strains of alkalophilic and/or industrial *Bacillus sp.*— in general—have been found to be non-transformable by competence and thus only subject to protoplast transformation which—as described above—is a very cumbersome method for introduction of DNA.

Examples of alkalophilic and/or industrial *Bacillus sp.* are given above.

Using an Auxotrophic Donor Cell

In another embodiment, the invention relates to a method of constructing a cell of a *Bacillus sp.* harbouring a DNA construct encoding a polypeptide of interest, in which method a population of auxotrophic modified bacterial donor cells harbouring i) a plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of unmarked *Bacillus sp.* recipient cells are mixed under conditions allowing the plasmid to be transferred from the population of the auxotrophic donor cells to the population of unmarked recipient cells by conjugation, and the auxotrophic property of the donor cell is exploited to select for recipient cells.

This aspect of the invention is clearly advantageous in that no selection need to be made for recipient cells—they are the only one remaining when exploiting the auxotrophic property of the donor cell.

The donor cell may, e.g., be auxotrophic for specific amino acids. A particular preferred donor to be used in a method of the present invention is a donor which is auxotrophic for D-alanine, i.e. a donor which is dal–. After the conjugation treatment has been accomplished the mixture of dal– donor cells and recipient cells is cultivated on or in a medium devoid of D-alamine, i.e. as medium in or on which the dal– donor cells are unable to grow. Thereby only recipient cells remain. The principle of using an auxotrophic marker is described in, e.g., U.S. Pat. No. 4,920,048.

Subsequently, only selection for recipient cells having acquired the DNA construct of interest must be made, conveniently by use of a selection marker, e.g. an antibiotic resistance, encoded by the plasmid.

Using a Curable Plasmid

In another aspect, the invention relates to a method of introducing a DNA construct encoding a polypeptide of interest into a cell of a *Bacillus sp.,* in which method a population of modified bacterial donor cells according to the present disclosure, the donor cells harbouring i) a curable plasmid comprising the DNA construct and at least one cis-acting DNA sequence required for the transfer of said plasmid by conjugation in the presence of a trans-acting mobilizing element, and ii) at least one DNA sequence encoding said trans-acting mobilizing element, and a population of *Bacillus sp.* recipient cells are mixed under conditions allowing the plasmid to be transferred from the population of donor cells to the population of recipient cells by conjugation.

The use of a curable plasmid is of particular relevance for the construction of recipient cells having received some elements of the plasmid which through conjugation has been transferred into the cell, but which is free from other elements such as the cis-acting DNA sequence required for the transfer of the plasmid by conjugation. In such cases it may be advantageous to integrate the DNA construct encoding a polypeptide of interest into the genome of the recipient cell, optionally together with other elements to be retained in the cell, whereas the elements which are not desired in the cell (such as the cis-acting DNA sequence) are retained on the plasmid. After genomic integration has taken place the cell is cured from the curable plasmid carrying the unwanted elements. Methods of achieving genomic integration is described further below.

The curable plasmid to be used in the method according to this aspect of the invention may be constructed by combining the respective elements (e.g. a temperature sensitive origin of replication, a cis-acting DNA sequence, a DNA construct of interest, etc.) in accordance with methods known in the art, typically by modification of either a curable plasmid or a plasmid carrying the cis-acting DNA sequence.

Preferred Embodiments of the Methods of the Invention

In the following, preferred embodiments of the above described methods of the invention are described. It is to be understood that the subject-matter of these embodiments of the invention are generally applicable for the method according to each and any of the main aspects dealt with above except if otherwise stated.

The Recipient Cell

It is preferred that the recipient cell to be used in any of the conjugation methods of the invention is a cell of an alkalophilic *Bacillus sp.* or a cell of an industrial *Bacillus sp.* The recipient cell may further be a cell of a *Bacillus sp.*, such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium* or *Bacillus thuringiensis*. The latter species may belong to the group of industrial or alkalophilic *Bacillus sp.*

The Modified Donor Cell

The modified bacterial donor cell to be used in any of the methods of the present invention may be a cell of an *Eschericia sp.*, such as *E. coli*, but is more preferably a cell of a *Bacillus sp.*, such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium* or *Bacillus thuringiensis.*, which cell, as compared to its parent cell, has a reduced capability or is incapable of producing a bactericidal agent which is normally produced by the parent cell, which modified cell harbours a i) a plasmid comprising a DNA construct encoding a polypeptide of interest and at least one cis-acting DNA sequence required for the transfer of said plasmid by conjugation in the presence of a trans-acting mobilizing element, and ii) at least one DNA sequence encoding said trans-acting mobilizing element.

Said cell is advantageously a cell of *B. subtilis*, e.g., *B. subtilis* 168 which has a low or no production of the bactericidal agent in question.

In a preferred embodiment, the cell has a reduced or no production of the bactericidal agent bacilysin or subtilosin or both of these agents.

Such cells are described in detail above in the section entitled "Conjugation by specific types of donor cells". In addition, the donor cell may be auxotrophic, e.g., as described in further detail above.

Curable Plasmid

In a highly preferred embodiment, the DNA construct to be introduced into the recipient cell is present on a curable plasmid which also comprises the cis-acting sequence is a curable plasmid. The curable plasmid and its use is further described above in the section entitled "Methods of the invention for DNA introduction by conjugation—using a curable plasmid".

Genomic Integration of the DNA Construct of Interest

Although the DNA construct encoding the polypeptide of interest, which is to be introduced in a recipient cell in accordance with any of the above described general aspects of the invention, may exist as an extrachromosomal element in the recipient cell (e.g., carried on the plasmid used for the introducing the DNA into the cell), it is generally preferred that the DNA construct be integrated in the genome of the recipient cell, since genomically integrated DNA is generally considered more stable.

The genomic integration may be achieved by well-known methods conveniently based on recombination between homologous sequences on the plasmid and the genome, respectively. In one embodiment genomic integration may be achieved when the plasmid to be transferred is a plasmid which comprises the following structure:

cis-R(1)-DNA-R(2), in which cis denotes the cis-acting DNA sequence required for conjugational transfer, DNA the DNA construct to be introduced into the recipient cell, and R(1) and R(2), respectively, a DNA sequence sufficiently homologous to a part of the recipient cell genome to allow for integration of the DNA construct located between R(1) and R(2) into the genome of the recipient cell by double crossing over.

The plasmid may conveniently be a curable plasmid, e.g., one which comprises a temperature sensitive origin of replication located on either side of the fragment comprising R(1)-DNA-R(2). The use of a curable plasmid has the additional advantage that it is possible to remove the cis-acting DNA sequence required for conjugation to take place from the cell once conjugation has taken place.

When a curable plasmid is used it is desirable that the method comprises the further step of selecting for recipient cells having integrated the DNA construct encoding a polypeptide of interest into the genome and from which the plasmid carrying the cis-acting element has been lost.

In connection with the embodiments of the present invention which relate to genomic integration by use of homologous regions, the term "homologous" region of the genome is preferably a region which is unessential for survival and proper functioning of the recipient cell.

Furthermore, as indicated above in order to improve the efficiency of the integration according to any of the above described methods one may utilise a curable plasmid. The plasmid may, for instance, be one which is temperature-sensitive for replication. Another way of increasing the efficiency of integration and subsequent loss of the first progeny vector from the cells may be to treat the cells transformed with the plasmid with a plasmid-curing agent, e.g., novobiocin (Gadó, I. et al., 1987. Zbl. Bakt. Hyg. A. 265, 136–145), after culturing the host cells under selective conditions as described above.

Amplification of the DNA Sequence Encoding a Polypeptide of Interest

The conjugation method of the invention may advantageously be used to achieve amplification of genomic DNA sequences present in the genome of the recipient cell. A very convenient method for achieving amplification of genomic DNA sequences is described in WO 94/14968, the contents of which are incorporated herein by reference. The genomic DNA sequence to be amplified may be the one encoding a polypeptide of interest, which has been introduced into the recipient cell by a conjugation method of the invention.

A Recipient Cell of the Invention

In a still further aspect the invention relates to a cell of a *Bacillus sp.* produced by a conjugation method of the invention which harbours a DNA construct of interest and a cis-acting DNA sequence required for the conjugation to take place. The cell is preferable of a cell of any of the *Bacillus sp.* specified above in the section entitled "Recipient cells".

A Method of Producing a Polypeptide

In a still further aspect the invention relates to a method of producing a polypeptide of interest, which method comprises cultivation of a cell produced by a method of the present invention as defined above under conditions conducive for the production of the polypeptide of interest, and optional recovery of the polypeptide of interest.

The polypeptide may be recovered by conventional recovery or purification techniques, examples of which are mentioned further above. The method in accordance with this aspect of the invention is particularly preferred for the production of translocated polypeptides, such as a secreted polypeptide or a polypeptide functioning in the secretory pathway of the recipient cell. Preferred examples of secreted polypeptides, such as enzymes, are mentioned above.

Plasmid and Construction of DNA Constructs

In a final aspect, the invention relates to a non-naturally occuring plasmid which comprises oriT or a functional part or analogue thereof. The plasmid may further comprise a DNA sequence conferring temperature sensitivity to the plasmid and/or a DNA construct encoding a polypeptide of interest, in particular a translocated polypeptide as defined above.

It will be understood that in order to function properly in the methods of the present invention the transacting element, such as orf-β, should be operably linked to regulatory DNA sequences (such as a promoter, a terminator, a ribosome binding site, etc.) ensuring that the gene be trancribed and translated. For instance, the gene should be preceeded by a suitable promoter, e.g. the one, which in nature is found to be associated with the gene, but more preferably a promoter ensuring a strong transcription from the gene. Furthermore, it may be advantageous to insert an extra promoter in front of the orf-β sequence. For instance, the insertion of the *B. amyloliquefaciens* alpha-amylase promoter in front of the orf-β and its natural promoter was found to result in a significantly improved transfer frequency. Examples of other strong promoters which may be inserted as extra or alternative promoters include the promoters of the *Bacillus licheniformis* a-amylase gene (amyL), the promoters of the *Bacillus stearothermophilus* maltogenic amylase gene (amyM), etc.

The DNA constructs and plasmids to be used in a method of the invention may be synthesized through a series of genetic manipulations employing methods and enzymes known in the art.

MATERIALS AND METHODS

| Bacterial strains and plasmids | |
|---|---|
| Donor strains: | |
| *B.subtilis* | |
| DN1280 | dal (ref.2) |
| PP289-5 | DN1280 (pLS20; tra⁺),(pBC16; Tcʳ) |
| MT101DN1280 | (pXO503; tra⁺ MLSʳ) |
| MT107DN1280 | (pXO503; tra⁺ MLSʳ)(pUB110; Kmʳ) |

| Bacterial strains and plasmids -continued | |
|---|---|
| 1A758 | 168 bac-1 (Bacillus Stock Center, Columbus, Ohio) |
| BW96 | 1A758 dalΔ |
| BW97 | 1A758 dalΔ::Camʳ(pXO503; tra+ MLSʳ) |
| BW98 | 1A758 dalΔ::kanʳ(pXO503; tra+ MLSʳ) |
| BW99 | 1A758 dalΔ(pPL2541-tet; Tetʳ) |
| BW100 | 1A758 dalΔ(pXO503; tra+ MLSʳ), (pPL2541-tet; Tetʳ) |
| BW101 | 1A758 dalΔ(pXO503; tra+ MLSʳ) |
| BW104 | 1A758 dalΔ(pSJ2662; Kanʳ) |
| BW105 | 1A758 dalΔ(pXO503; tra+ MLSʳ), (pSJ2662; Kanʳ) |
| BW106 | 1A758 dalΔ::Kanʳ(pXO503; tra+ MLSʳ), (pMOL913; Camʳ) |
| Recipient strains: | |
| *B.subtilis* W23 | BGSC |
| *B.lentus* C360 | (ref.3) |
| *B.licheniformis* ATCC 102 | |
| *B.lentus* strain 165-2 | |
| *B.amyloliquefaciens* | |
| Plasmids: | |
| pUB110 Mob⁺ Kmʳ | BGSC |
| pBC16Mob⁺ Tcʳ | (ref.4) |
| pLS20 Tra⁺ | (ref.1) |
| pXO503 | Tra⁺ MLSʳ (pLS20::Tn917, 60 kb)(ref.1) |
| pPL2541-tet | Mob⁺ Tetʳ (pE194 ts ori) |
| pSJ2662 | Mob⁺ Kmʳ (pUB110 with polylinker) |
| pMOL913 | Mob⁺ Cmʳ (pUB110 w/cat replacing neo gene) |

Media and growth conditions. The conjugation methods is a modified version of the methods described by Koehler and Thorne (ref.1). All bacteria strains were routinely grown on LB agar plates (Maniatis, T et all 1982 ref 5), supplemented as appropriate with D-alanine (50 μg/l) and antibiotics. (For better growth of the alkalophile strains the LB media could be buffered with 50 mM $NaHCO_3$). Freshly made over night cultures were used for conjugation.

Matings. Overnight cultures (14–24 hr) of donor and recipient strains were transferred to LB+D-alanine plates, and an inoculum containing 5–10 colonies of each strain were mixed. After mixing the strains, the cells were spread over the hole plate. The matings were incubated for at least 4 hr at 30°–37° C. The mating plates were either replicated to selective plates (=LB agar with the appropriate antibiotics but without D-alanine) or the cells were resuspended in LB media and spread in dilutions up to $10^5$ on selective plates. From these plates conjugants were scored after 1 to 2 days at 30°–37° C. and further purified on selective plates.

ref.1 Koehler, T. M., Thorne, C. B., 1987, J. Bact vol 169, 11 p. 5271–5278 ref.2 Diderichsen, B., 1987. In Bacillus Molecular genetics and biotechnology applications. p. 35–46.

ref.3 Aunstrup, K., H. Outtrup, O. Andresen and C. Dampmann. 1972. Proteases from alkalophilic *Bacillus* spiecies. p. 299–305. In Proceedings of the fourth international symposium on fermentation technology. Society of fermentations technology, Osaka, Japan.

ref.4 Bernhard, K., H. Schrempf and W. Goebel. 1978. Bacteriocin and antibiotic resistance plasmids in *B. cerius* and *B. subtilis*. J. Bacteriol. 133, 897–903.

ref.5 Maniatis, T et all 1982. Molecular cloning: A laboratory manual. Cold Spring Harbor Laboratory, Cold Spring Harbor, N.Y.). the mating plates were either replicated to selective plates (=LB agar with the appropriate antibiotics but without D-alanine) or the cells were resuspended in LB media and spread in dilutions up to $10^5$ on selective plates. From these plates conjugants were scored after 1 to 2 days at 30°–37° C. and further purified on selective plates.

EXAMPLE 1

A) Construction of a Temperature-Sensitive Transposon-Delivery Vector Encoding SAVINASE®

SAVINASE® (Novo Nordisk A/S, Bagsvaerd, Denmark) is an extracellular, alkaline protease from *Bacillus lentus*. A vector expressing SAVINASE® and useful for the delivery of this gene by transposition is pMOL553. This plasmid was constructed in two steps.

Step 1

A BamHI site was introduced into the transposon of pHV1248 (Petit, M.-A., Bruand, C., Janniere, L. Ehrlich, S. D. (1990). Tn10-derived transposons active in *Bacillus subtilis, J. Bacteriol.*, 172:6736–6740) immediately upstream of the cat gene. The BamHI site was inserted by use of the PCR based SOE technique described earlier (Horton, R. M. et al. (1989) Gene, pp. 61–68). Two separate PCR reactions were performed using the pHV1248 plasmid as template. The oligos for the first PCR reaction were primer 1: CCCACTGGATCCAATTTTCGTTTGTTG (SEQ ID NO:1) and primer 2: GCAAATTGATCCAAGAGAAC-CAAC (SEQ ID NO:2). The underlined based in primer 1 show the position of the BamHI site. The second PCR reaction was based on primer 3: CAACAAACGAAAAT-TGGATCCAGTGGG (SEQ ID NO:3) and primer 4: GCA-CATCATCATCATAAGC (SEQ ID NO:4). Both PCR reactions were performed by standard procedures using temperatures of 96° C. at denaturation, 55° C. at annealing and 72° C. at the extension step. A total of 20 cycles were performed. Both fragments were purified from an agarose gel and 500 ng of each were used for a second 5 cycle PCR reaction: 96° C. for 2 min., 50° C. for 5 min and 72° C. for 1 min. Primer 2 and primer 4 (100 pmol) were added at 96° C. and a third 25 cycle PCR reaction was initiated: 96° C. for 30 sec., 55° C. for 30 sec. and 72° C. for 90 sec. The final PCR fragment of 1330 bp was digested with HindIII and cloned back into the HindIII digested pHV1248 giving the plasmid pMOL610. The ligation mixture was transformed into *E. coli* SJ2 (Diderichsen et al., 190, J. Bacteriol. 172, 4315–4321). The position of the BamHI site in pMOL610 was verified by restriction digest.

Step 2

In this step the entire SAVINASE® gene was cloned into the BamHI site of pMOL610. The total SAVINASE® gene and promoter region was amplified from a pSX222 (WO 92/11357) plasmid by PCR using primers with BamHI restriction sites (underlined) 5: CCGGCGGATC-CAAGGGGTGATCG (SEQ ID NO:5) and primer 6: GGGGTACTAGTAACCCGGGCCCGGCGTA-GAGGATCCATACACAAA (SEQ ID NO:6). The PCR reaction was performed as follows: 96° C. for 30 sec., 55° C. for 30 sec., and 72° C. for 120 sec. After 20 cycles the PCR fragment was BamHI digested, purified and cloned into the BamHI site of pMOL610. The cloning was verified by restriction digests and a distinct protease phenotype in *B. subtilis* (e.g., in strain DN1885, (Diderichsen et al., 1990, J. Bacteriol. 172, 4315–4321.), or protease-deficient derivatives of this strain). The vector encoding SAVINASE® thus constructed is pMOL553.

B) Construction of a Mobilizable Transposon Delivery Vector Encoding SAVINASE®

Mobilization of plasmid pUB110 by pLS20 or its derivatives has been described and analyzed in some details (Koehler, T. M. and Thorne, C. B. (1987). *Bacillus subtilis* (*natto*) plasmid pLS20 mediates interspecies plasmid transfer. J. Bacteriol., 169, 5271–5278; Selinger, L. B., McGregor, N. F., Khachatourians, G. G. and Hynes, M. F. (1990). Mobilization of closely related plasmids pUB110 and pBC16 by Bacillus plasmid pXO503 requires trans-acting open reading frame β. J. Bacteriol., 172, 3290–3297). We have used elements from these plasmids to mobilize the SAVINASE® -expressing trans-poson delivery vector.

Mobilization of pUB110 is dependent on a cis acting region (oriT) located 5' to orfβ (Selinger et al., 1990). A 555 bp segment from pUB110, extending from pos. 1020 to pos. 1575 in the pUB110 sequence, was PCR amplified using primers LWN5232 and LWN5233.

LWN5232:

5'-GTCGGAGCTCATTATTAATCTGTTCAGCAATCGGGC-3'
(SEQ ID NO:7)

LWN5233:

5'-GTCGGAGCTCTGCCTTTTAGTCCAGCTGATTTCAC-3'
(SEQ ID NO:8)

The amplified fragment was digested with SacI and initially cloned into the SacI site of an *E. coli* plasmid (a pUC19 derivative). The fragment was subsequently excised again using SacI, and cloned into the unique SacI site in the previously described plasmid pMOL553. The ligation mixture was transformed into *E. coli* SJ2 selecting Amp resistance. The resulting plasmid is pMOL553-oriT.

C) Construction of a Conjugative Donor Strain Containing a Mobilizable Transposon Delivery Vector Encoding SAVINASE®

Plasmids pLS20 and pBC16 can be transferred by conjugation from *B. subtilis* strain PSL1 UM13 into various Bacillus recipient strains (Koehler and Thorne, 1987). DNA1280 is a derivative of *B. subtilis* 168, containing a deletion in the dal gene (Diderichsen, B. (1986). A genetic system for stabilization of cloned genes in *Bacillus subtilis*, p35–46. In A. T. Ganesan and J. A. Hoch (eds.), Bacillus molecular genetics and biotechnology applications. Academic Press, Inc., New York). DN1280 was rendered competent and transformed with plasmid pHV1248, selecting erythromycin resistance (5 µg/ml) at 30° C. The resulting strain was used as recipient in conjugation with PSL1 UM13. Both strains were mixed on an LB plate supplemented with phosphate (0.01M $K_3PO_4$), glucose (0.4%), starch (0.5%) and D-alanine (100 µg/ml), and incubated for 5 hours at 30° C. the plate was then replicated onto an LB plate as above, but in addition contained erythromycin (5 µg/ml) and tetracycline (5 µg/ml).

Single colonies appearing on the replica plate was assayed for their ability to transfer pBC16 into *B. subtilis* DN1885. Conjugation was performed by mixing of the strains on LB plates as above and incubation for 5 hours at 30° C. Replication was to LB plates with tetracycline (5 µg/ml), but without D-alanine.

The omission of D-alanine effectively counterselects the dal– donor strain. A few of the colonies assayed were able to transfer the Tet$^R$ marker into DN1885. This indicates that these colonies harbour pLS20 in addition to pBC16. One such colony was propagated at 50° C. in liquid TY medium containing tetracycline (5 µg/ml) and D-alanine (100 µg/ml), subsequently plated on LB containing tetracycline (5 µg/ml) and D-alanine (100 µg/ml), and replica plated onto LB containing D-alanine (100 µg/ml) and erythromycin (5 µg/ml) or chloramphenicol (6 µg/ml), respectively. A tetracycline resistant, erythromycin and chloramphenicol sensitive isolate was kept at PP289-5. This strain, which is dal– and contains pLS20 and pBC16, can serve as a conjugation donor strain that allows the transfer of plasmids containing the pUB110 oriT into various recipient strains.

Accordingly, PP289-5 was rendered competent and transformed with the oriT containing derivative of pMOL553, pMOL553-oriT. Plasmids were prepared from the pooled transformants of *E. coli* SJ2, and the plasmid mixtures transformed into PP289-5, selecting resistance to tetracycline (5 µg/ml), chloramphenicol (6 µg/ml) and erythromycin (5 µg/ml) on LB plates containing D-alanine (100 µg/ml). The transformants were again pooled, and the pool used to transfer pMOL553-oriT into DN1885 by conjugation, using the method described above. Finally, the identity of the plasmids in the transconjugants were verified by restriction mapping, and a correct plasmid was kept (pMOL553-oriT). pMOL553-oriT was retransformed into PP289-5 for further use.

D) Conjugative Transfer of an Alkaline Protease Gene into an Alkalophilic Bacillus Strain PP289-5 containing pMOL553-oriT was used as a conjugation donor strain to transfer a homologous apr gene, encoding SAVINASE®, isolated from *Bacillus lentus*, into the alkalophile *Bacillus lentus* strain C360 (Aunstrup, K., Outtrup, H., Andresen, O., Dampmann, C. (1972) Proteases from alkalophilic *Bacillus* species, p. 299–305. In Proceedings of the fourth international symposium on fermentation technology. Society of fermentation technology, Osaka, Japan).

One day old cells of the donor strain PP289-5/pMOL553-oriT were harvested from an LB plate supplemented with 50 µg/ml D-alanine, 5 µg/ml erythromycin, and 5 µg/ml tetracyclin. The recipient strain (C360) was harvested (one day old cells) from a LB9 plate (LB9=LB plate buffered to pH9 by 0.05M $HNa_2CO_3/H_2NaCO_3$).

The recipient and the donor strains were mixed on LB plates supplemented with 50 µg/ml D-alanine, and incubated for 5 hours at 30° C. The plate was then replicated onto an LB9 plate supplemented with 5 µg/ml erythromycin. Single colonies appearing on the replica plate (after 2 days at 30° C.) were reisolated on an LB9 plate supplemented with 5 µg/ml erythromycin. (By omitting the D-alanine in the selective plates the dal– donor strain is killed and only the *B. lentus* recipient containing the mobilizable pMOL553-oriT plasmid will survive). The plasmids in several transconjugants of *B. lentus* were isolated and a restriction mapping confirmed the transfer of the pMOL553-oriT plasmid into *B. lentus*.

EXAMPLE 2
Construction of New bac-1 Donor Strain(s)

The dal gene was deleted from *Bacillus subtilis* strain 1A758 (Bacillus Stock Center, Columbus, Ohio) to permit counterselection against the strain following conjugation. *Bacillus subtilis* strain 1A758 has a mutation in the "bac-1" locus which abolishes the ability of the bacterium to synthesize the dipeptide antibiotic bacilysin. A deleted version of the dal gene was constructed in vitro which could be exchanged for the wild-type dal gene on the bacterial chromosome. The 5' and 3' portions of the dal gene were cloned by PCR using oligos 1 and 2 which were used to PCR amplify the 5' portion of the gene (nucleotides 19–419, the A of the ATG codon is +1) and oligos 3 and 4 were used to PCR amplify the 3' portion of the gene (nucleotides 618–1037).

Oligo 1: 5'-GAGCTCACAGAGATACGTGGGC-3'(SEQ ID NO:9)

Oligo 2: 5'-GGATCCACACCAAGTCTGTTCAT-3'(SEQ ID NO:10)

Oligo 3: 5'-GGATCCGCTGGACTCCGGCTG-3'(SEQ ID NO:11)

Oligo 4: 5'-AAGCTTATCTCATCCATGGAAA-3'(SEQ ID NO:12)

Both PCR products were cloned into the pCRII vector using the TA Cloning kit (Invitrogen, Corp., San Diego, Calif). Once cloned, the two halves were combined in vitro by utilizing the BamHI site common to both fragments to yield a partial dal gene (Δdal) with a ~200bp deletion in the middle which can be conveniently removed from the pCRII vector as a NotI-HindIII fragment (the NotI site is part of the vector polylinker).

Two different methods were used to generate a dal–bac-1 donor strain. The first involved creating a gene disruption by inserting a cat gene into the dal gene coding sequence. A cat expression cassette was cloned into the BamHI site of the pCRII-Δdal plasmid. This construction was introduced into the bacterial chromosome via a double cross-over in the following manner; the plasmid was linearized with ScaI and transformed into the bac-1 strain containing the conjugation plasmid pXO503, selecting for chloramphenicol resistance on TBAB (Tryptone blood agar base) plates containing D-alanine (0.1 mg/ml) and chloramphenicol (5 µg/ml). The only way for the bacterial cells to acquire chloramphenicol resistance was for a double cross-over to occur between the dal sequences flanking the cat gene of the linear plasmid DNA and the chromosome, thereby introducing the disrupted dal gene containing the cat expression cassette. This procedure yielded strain *Bacillus subtilis* BW97, a bac-1, Δdal::cat conjugation proficient donor strain.

A second method was used to construct an "unmarked" donor strain (no antibiotic resistance marker inserted into the dal gene). In this case, instead of selecting directly for a double cross-over event, two separate single cross-overs were performed in order to introduce a deleted "unmarked" dal gene into the bacterial chromosome. This was accomplished as follows: the deleted dal gene (described above) was cloned into the NotI-HindIII site of the temperature sensitive plasmid pE194$^{ts}$, transformed into the bac-1 strain, and grown at the permissive temperature of 34° C. In order to obtain the first cross-over (integration of the dal deletion plasmid into the dal gene on the chromosome), the transformed strain was streaked onto a TBAB plate containing D-alanine (0.1 mg/ml) (required for cell growth, as integration into the chromosome disrupts the dal gene) and erythromycin (5 µg/ml) and grown overnight at the non-permissive temperature of 45° C. A large colony was restreaked under the same conditions yielding a homogeneous population of cells containing the temperature-sensitive plasmid integrated into the dal gene on the chromosome. At the non-permissive temperature, only cells which contain the plasmid in the chromosome were capable of growing on erythromycin since the plasmid was incapable of replicating. In order to obtain the second cross-over event (resulting in excision of the plasmid from the chromosome leaving behind the deleted version of the dal gene), a loopful of cells was transferred to 20 ml of Luria broth supplemented with D-alanine (0.1 mg/ml) and grown to late log phase without selection at the permissive temperature of 34° C. to permit function of the origin of replication and occurrence of the second cross-over event. Cells were transferred 4 times more (1/100 dilution each transfer) to allow the plasmid to excise from the chromosome and segregate out of the population. Finally, cells were plated for single colonies at 34° C. on TBAB plates supplemented with D-alanine (0.1 mg/ml) and replica-plated onto TBAB plates without D-alanine (0.1 mg/ml) and TBAB plates with D-alanine (0.1 mg/ml) and erythromycin (5 µg/ml) to score colonies which were dal– and erm$^s$. Two out of 50colonies yielded this phenotype. The resulting strain was designated *Bacillus subtilis* BW96. Plasmid pSJ2662 (essentially pUB110 with a polylinker inserted into a non-essential region) was then introduced to yield the dalΔ bac-1, kan$^r$ strain BW104. The conjugation plasmid pXO503 was introduced into this train by conjugation using BW100 as the donor strain; transconjugants were scored by selecting for growth on TBAB+D-alanine+erythromycin (5 µg/ml)+kanamycin (10 µg/ml). This yielded the "unmarked" donor strain BW105: bac-1, dalΔ containing pXO503 and pSJ2662.

The donor strain BW101 (a dal deleted strain harboring only pXO503) was constructed by first introducing the ts replicon pPL2541-tet into BW96 yielding the dal deleted, bac-1, tet' strain BW99. The conjugation plasmid pXO503 was introduced into this strain by conjugation using BW97 as the donor strain; transconjugants were scored by selecting for growth on TBAB+D-alanine+erythromycin (5 µg/ml)+ tetracycline (10 µg/ml). This yielded the donor strain BW100: bac-1, dalΔ containing pXO503 and pPL2541-tet. Finally, this strain was propogated overnight at the nonpermissive temperature of 45° C. and plated for single colonies on TBAB+D-alanine at the permissive temperature of 34° C. Colonies were then patched onto TBAB+D-alanine+tetracycline (10 µg/ml) plates and TBAB+D-alanine+erythromycin (5 µg/ml) to identify colonies which were erm$^r$ and tet$^s$; several colonies exhibiting this phenotype were identified, one was saved and designated BW101.

A) Conjugation into a *B. amyloliquefaciens* Strain

Strain BW105 was tested for its ability to mobilize pSJ2662 into *B. amyloliquefaciens* (and *B. subtilis* 168 as a positive control); this donor was compared to the equivalent wild-type donor strain MT105. Both donors and recipients were grown in 2 ml of L broth+D-alanine+glucose (0.2%) to mid-log phase. One ml of the donor and recipient were mixed and centrifuged, the pellets were resuspended in 100 ul of residual broth; 50 ul was then spotted onto a TBAB+D-alanine+glucose plate. They were incubated for 5 hours at 37° C.; the cells were scraped from the plate and transferred to 1 ml of L broth and titered transconjugants on TBAB+ neomycin (10 µg/ml) plates and for viable cells on plain TBAB plates. Both donors mobilized the pUB110 replicon at comparably high efficiencies into *B. subtilis* ($10^{-3}$–$10^{-4}$). However, the bac-1 donor strain was much better (>100-fold) at mobilizing pUB110into the *B. amyloliquefaciens* strain (~$10^{-5}$) in comparison to the MT105 donor (<$10^{-7}$)

B) Conjugation into *B. lentus* Strain 165-2

The bac-1 donor strain BW97 with a cat insertion in the dal gene (bac-1, dalΔ::cam$^r$) was transformed with plasmid pCm::Nm. This plasmid, obtained from the Bacillus Genetic Stock Center, contains the neo resistance gene flanked by the 5' and 3' portions of the cat gene. Transformation with this plasmid can replace the cat gene in the dal gene with the neo gene. Transformation with this plasmid resulted in hundreds of neo resistant colonies. Since the plasmid is on a pE194 replicon, one of the tranformants was grown at the non-permissive temperature (45° C.) to integrate the plasmid in the chromosome via homologous recombination. The strain was grown at the permissive temperature (34° C.) for about 20 generations, then plated onto TBAB+neo. Out of 30 neo resistant colonies, 2 were chloramphenicol sensitive, indicating the replacement of the cat gene with the neo gene. This strain BW98 (bac-1, dalΔ::neo$^r$) was then tranformed with plasmid pMOL913 which is essentially pUB110 with the cat gene instead of neo. A chloramphenicol resistant colony was chosen as a donor strain (BW106) and compared with the bac+ equivalent (MT101/pMOL913). Conjugations were performed as described above. All conjugations were done at pH7. The number of transconjugants obtained with the old donor were about 10–100 per experiment, while using the new donor approximately $10^3$–$10^4$ total transconjugants were obtained. The selection was done at pH7, but all transconjugants were tested for the ability to grow at pH9, all grew indicating they were *B. lentus*.

Using the old donor strain containing pUB110(MT105) in a conjugation with *B. lentus*, no transconjugants were obtained selecting for neomycin resistance at pH7. Using the equivalent new donor strain, approximately $10^3$ total transconjugants were obtained selecting for neo resistance at pH7, no colonies were obtained when plating out the donor alone or recipient alone. All of these colonies grew at pH9, confirming they are correct.

C) Isolation of *B. subtillis* Mutants with Reduced Killing Potential

Even though the bac-1 mutant strain of *B. subtilis* almost eliminates killing of *B. amyloliquefaciens* recipient cells, there is still detectable killing of some other *Bacillus* species such as *B. megaterium*, implying the other antimicrobial agents are being produced. In the following it is shown that it is feasible to "knockout" these other factors by classical mutagenesis schemes, possibly combining one or more mutations with the bac-1 mutant and generating even better donor strains. A mutagenesis program was undertaken to obtain additional mutants, cells of the wild-type donor strain MT101 were mutagenised with the chemical mutagen EMS (other forms of mutagenesis such as NTG, UV, and transposon tagging could also be used). A 0.5 ml overnight culture of MT101 grown in Spizizen's I media+D-alanine was used to inoculate 20 ml of the same media in a side armed Klett flask. Cells were grown with shaking at 37° C. to 70 Klett units and centrifuged at room temperature. The cell pellet was resuspended in 12 ml of Spizizen salts+2.5 ml 1M Tris ph 7.4. For the $t_0$ sample a 2 ml aliquot was transferred to 18 ml or VY media+D-alanine and shaken overnight at 37° C. To the remainder 30 µl of EMS was added and the cells were shaken at 37° C.; 2 ml aliquots were taken at $t_1$ (1 hour), $t_2$ (2 hour), and $t_3$ (3 hour), transferred to fresh media as described above for the $t_0$ sample. After the overnight incubation glycerol was added to the cells to 15% final concentration, titrated, and stored at -70° C. in a Revco freezer; the % survival was 38, 19, and 0.1 for samples $t_1$, $t_2$, and $t_3$ respectively.

The $t_2$ sample was chosen for mutant screening. Cells were plated for single colonies on TBAB+D-alanine; these were then replica plated onto a freshly spread lawn of the *B. amyloliquefaciens* recipient strain (any "sensitive" strain could be used as an indicator). These plates were incubated overnight at 34° C. and scored for clearing zones around the MT101 donor colonies; potential mutants had substantially reduced or no zones of clearing. Six mutants were obtained out of ~1500 colonies examined; one of these, "mut1", was selected for further analysis. Both the *B. amyloliquefaciens* and the mut1 strains were grown to mid-log phase, one ml of each was combined and pelleted by centrifugation, cells were resuspended in 100 µl of broth and 50 µl was spotted onto a TBAB+D-alanine plate. After 5 hours of incubation at 37° C., the cells were scraped from the plate surface and resuspended into 1 ml of fresh L broth; survivers were titrated by plating dilutions onto TBAB plates lacking D-alanine. Killing was found to be substantially reduced (10,000-fold) in comparison to the wild-type donor.

What is claimed is:

1. A modified Bacillus donor cell for conjugative transfer of a plasmid to a recipient Bacillus cell, wherein the modified donor cell has a reduced capacity of producing a bactericidal agent compared to the parent Bacillus cell of the modified Bacillus donor cell, in which the bactericidal agent kills or prevents the growth of the recipient Bacillus cell, and wherein the modified donor cell comprises:

(a) a plasmid comprising a DNA construct encoding a polypeptide wherein the plasmid is to be transferred by conjugation from the modified donor cell to the recipient cell;

(b) at least one cis-acting DNA sequence required for the conjugative transfer of the plasmid in the presence of a trans-acting mobilizing element to the recipient cell;

(c) at least one DNA sequence encoding the trans-acting mobilizing element; and (d) a conjugative plasmid which mediates the conjugative transfer of the plasmid from the modified donor cell to the recipient cell.

2. The donor cell of claim 1 which has a reduced capacity of producing two or more different bactericidal agents compared to the parent donor cell.

3. The donor cell of claim 1 which does not produce the bactericidal agent.

4. The donor cell of claim 1, wherein the bactericidal agent is bacilysin or subtilosin.

5. The donor cell of claim 1, wherein the recipient cell is an alkalophilic Bacillus.

6. The donor cell of claim 1, wherein the recipient cell is an industrial Bacillus.

7. The donor cell of claim 1, wherein the cis-acting DNA sequence is oriT.

8. The donor cell of claim 1, wherein the trans-acting element is orf-$\beta$.

9. The donor cell of claim 1, wherein the DNA sequence encoding the trans-acting mobilizing element is present on a second plasmid or in the genome of the donor cell.

10. The donor cell of claim 1, wherein the cis-acting DNA sequence is contained on a curable plasmid.

11. The donor cell of claim 1, wherein the conjugative plasmid is pLS20 or a derivative thereof having retained the conjugative capability of pLS20.

12. A method for making the donor cell of claim 1 which comprises subjecting a parent Bacillus cell to mutagenesis and screening for a mutant donor cell which exhibits a lower degree of killing of the recipient cell compared to the parent cell or no killing of the recipient cell.

13. The donor cell of claim 1, wherein the polypeptide is a translocated polypeptide.

14. The donor cell of claim 13, wherein the translocated polypeptide is a secreted polypeptide or a polypeptide of the secretory pathway of a secreting cell.

15. The donor cell of claim 14, wherein the secreted polypeptide is an enzyme.

16. The donor cell of claim 14, wherein the secretory pathway polypeptide is PrsA.

17. The donor cell of claim 1 which is auxotrophic.

18. The donor cell of claim 17 which is auxotrophic for an amino acid.

19. A method of introducing a DNA construct encoding a polypeptide into a Bacillus cell, said method comprising:

(A) mixing (i) a population of modified Bacillus donor cells comprising (a) a plasmid comprising a DNA construct encoding a polypeptide wherein the plasmid is to be transferred by conjugation from the modified donor cell to the recipient cell, (b) at least one cis-acting DNA sequence required for the conjugative transfer of the plasmid in the presence of a trans-acting mobilizing element to the recipient cell, (c) at least one DNA sequence encoding the trans-acting mobilizing element, and (d) a conjugative plasmid which mediates the conjugative transfer of the plasmid from the modified donor cell to the recipient cell, with (ii) a population of Bacillus recipient cells under conditions allowing the plasmid to be transferred by conjugation from the population of donor cells to the population of recipient cells;

wherein the modified donor cell has a reduced capacity of producing a bactericidal agent compared to a parent donor cell, in which the bactericidal agent kills or prevents the growth of the recipient Bacillus cell; and (B) selecting a recipient cell comprising the DNA construct.

20. The method of claim 19, wherein the recipient cell is an alkalophilic Bacillus.

21. The method of claim 19, wherein the recipient cell is an industrial Bacillus.

22. The method of claim 19, wherein the plasmid is a curable plasmid comprising the DNA construct.

23. The method of claim 19, wherein the population of modified donor cells are auxotrophic cells and wherein the recipient cell is selected by exploiting the auxotrophic property of the donor cell.

24. The method of claim 23, wherein the auxotrophic property of the donor cell is dal$^-$.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

CCCACTGGAT CCAATTTTCG TTTGTTG      27

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCAAATTGAT CCAAGAGAAC CAAC      24

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CAACAAACGA AAATTGGATC CAGTGGG      27

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCACATCATC ATCATAAG      18

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCGGCGGATC CAAGGGGTGA TCG      23

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GGGGTACTAG TAACCCGGGC CCGGCGTAGA GGATCCATAC ACAAA      45

( 2 ) INFORMATION FOR SEQ ID NO:7:

( i ) SEQUENCE CHARACTERISTICS:
        ( A ) LENGTH: 36 base pairs

-continued

```
            ( B ) TYPE: nucleic acid
            ( C ) STRANDEDNESS: single
            ( D ) TOPOLOGY: linear ( x i ) SEQUENCE DESCRIPTION: SEQ ID NO:7:

GTCGGAGCTC  ATTATTAATC  TGTTCAGCAA  TCGGGC                              3 6

( 2 ) INFORMATION FOR SEQ ID NO:8:

( i ) SEQUENCE CHARACTERISTICS:
            ( A ) LENGTH: 35 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:8:

GTCGGAGCTC  TGCCTTTTAG  TCCAGCTGAT  TTCAC                               3 5

( 2 ) INFORMATION FOR SEQ ID NO:9:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:9:

GAGCTCACAG  AGATACGTGG  GC                                              2 2

( 2 ) INFORMATION FOR SEQ ID NO:10:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:10:

GGATCCACAC  CAAGTCTGTT  CAT                                             2 3

( 2 ) INFORMATION FOR SEQ ID NO:11:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:11:

GGATCCGCTG  GACTCCGGCT  G                                               2 1

( 2 ) INFORMATION FOR SEQ ID NO:12:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:12:

AAGCTTATCT  CATCCATGGA  AA                                              2 2
```